United States Patent
Song et al.

(10) Patent No.: US 8,222,476 B2
(45) Date of Patent: Jul. 17, 2012

(54) ABSORBENT ARTICLES WITH IMPENDING LEAKAGE SENSORS

(75) Inventors: Xuedong Song, Alpharetta, GA (US);
Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 550 days.

(21) Appl. No.: 12/262,784

(22) Filed: Oct. 31, 2008

(65) Prior Publication Data

US 2010/0114047 A1 May 6, 2010

(51) Int. Cl.
A61F 13/15 (2006.01)

(52) U.S. Cl. ......... 604/361; 604/359; 604/362; 604/367

(58) Field of Classification Search .................. 604/361, 604/359, 362, 367
See application file for complete search history.

(56) References Cited

U.S. PATENT DOCUMENTS

| | | |
|---|---|---|
| 4,022,211 A | 5/1977 | Timmons et al. |
| 4,704,116 A | 11/1987 | Enloe |
| 4,834,733 A | 5/1989 | Huntoon et al. |
| 5,003,178 A | 3/1991 | Livesay |
| 5,192,606 A | 3/1993 | Proxmire et al. |
| 5,354,289 A | 10/1994 | Mitchell et al. |
| H1376 H | 11/1994 | Osborn, III et al. |
| 5,399,219 A | 3/1995 | Roessler et al. |
| 5,486,166 A | 1/1996 | Bishop et al. |
| 5,490,846 A | 2/1996 | Ellis et al. |
| 5,540,796 A | 7/1996 | Fries |
| 5,595,618 A | 1/1997 | Fries et al. |
| 5,702,377 A | 12/1997 | Collier et al. |
| 5,931,823 A | 8/1999 | Stokes et al. |
| 5,962,995 A | 10/1999 | Avnery |
| 6,060,638 A | 5/2000 | Paul et al. |
| 6,066,774 A * | 5/2000 | Roe .............................. 604/361 |
| 6,093,869 A * | 7/2000 | Roe et al. ...................... 604/361 |
| 6,150,002 A | 11/2000 | Varona |
| 6,407,492 B1 | 6/2002 | Avnery et al. |
| 6,486,227 B2 | 11/2002 | Nohr et al. |

(Continued)

FOREIGN PATENT DOCUMENTS

| | | |
|---|---|---|
| DE | 93 09 199 | 10/1993 |
| EP | 0 727 975 | 8/1996 |
| EP | 1 023 024 | 8/2000 |
| KR | 10-0484478 | 8/2005 |
| WO | WO 91/19471 | 12/1991 |
| WO | 95/16425 | 6/1995 |
| WO | WO 99/20216 | 4/1999 |
| WO | WO 01/95845 | 12/2001 |
| WO | WO 2007/087674 | 8/2007 |

OTHER PUBLICATIONS

International Search Report & Written Opinion for PCT/IB2009/053880—6 pages.

*Primary Examiner* — Jacqueline F. Stephens (74) *Attorney, Agent, or Firm* — Dority & Manning, P.A.

(57) ABSTRACT

In accordance with one embodiment of the present disclosure an absorbent article capable of indicating the presence or absence of urine as well as impending leakage of urine is disclosed. The absorbent article includes a substantially liquid impermeable layer, a liquid permeable layer, and an absorbent core positioned between the substantially liquid impermeable layer and the liquid permeable layer. A plurality of sensors are integrated into the article across the width of the article and positioned such that the sensors are in fluid communication with urine when provided by a wearer of the article. At least one of the sensors comprises a pH indicator. At least one of the sensors is capable of indicating the presence or absence of urine and at least one of the sensors is capable of indicating impending leakage of urine from the article.

20 Claims, 3 Drawing Sheets

U.S. PATENT DOCUMENTS

| | | |
|---|---|---|
| 6,617,488 B1 | 9/2003 | Springer et al. |
| 6,663,611 B2 | 12/2003 | Blaney et al. |
| 6,710,221 B1 | 3/2004 | Pierce et al. |
| 6,780,896 B2 | 8/2004 | MacDonald et al. |
| 2002/0026164 A1 | 2/2002 | Roy et al. |
| 2004/0102750 A1 | 5/2004 | Jameson |
| 2005/0054255 A1 | 3/2005 | Morman et al. |
| 2005/0059941 A1 | 3/2005 | Baldwin et al. |
| 2006/0229578 A1 | 10/2006 | Roe et al. |
| 2008/0021423 A1 | 1/2008 | Klofta et al. |
| 2008/0147030 A1 | 6/2008 | Nhan et al. |
| 2008/0147031 A1* | 6/2008 | Long et al. .................... 604/361 |

* cited by examiner

ABSORBENT ARTICLES WITH IMPENDING LEAKAGE SENSORS

BACKGROUND

Disposable absorbent articles such as diapers, training pants, incontinence pads, and the like are highly absorbent and efficiently pull moisture away from the wearer, reducing skin irritation caused by prolonged wetness exposure. Because these articles are so absorbent, wearers may not realize they have urinated, particularly if they are inexperienced toddlers who may not recognize the meaning of body sensations associated with urination. As a result, visual mechanisms have been employed to signal the presence of wetness in absorbent articles. There are a large number of wetness sensing technologies that currently exist including electronic-based wetness sensors, color-based wetness sensors, and enzyme-based wetness sensors.

However, such conventional sensors are designed to be triggered after only a single urination event. Certain consumers are reluctant to change absorbent articles until after they reach full absorbent capacity. Thus, although the presence or absence of urine may be detected with conventional sensors, the remaining absorbent capacity of the article is unknown. As a result, consumers are left guessing as to whether the absorbent article requires changing or whether absorbent capacity remains. This uncertainty may lead the consumer to continue to use the absorbent article until the article wets beyond its absorbent capacity. This can ultimately result in leakage before the article is changed, which is undesirable.

Thus, a need exists for an absorbent article that includes sensors which can indicate impending leakage. A method of utilizing such an absorbent article would also be beneficial.

SUMMARY

In accordance with one embodiment of the present disclosure an absorbent article capable of indicating the presence or absence of urine as well as impending leakage of urine is disclosed. The absorbent article includes a substantially liquid impermeable layer, a liquid permeable layer, and an absorbent core positioned between the substantially liquid impermeable layer and the liquid permeable layer. A plurality of sensors are integrated into the article across the width of the article and positioned such that the sensors are in fluid communication with urine when provided by a wearer of the article. At least one of the sensors comprises a pH indicator. At least one of the sensors is capable of indicating the presence or absence of urine and at least one of the sensors is capable of indicating impending leakage of urine from the article.

In another embodiment of the present disclosure, a method for detecting the presence or absence of urine as well as impending leakage of urine in an absorbent article is disclosed. The method includes contacting urine with an absorbent article having a plurality of sensors integrated therein. At least one of the sensors comprises a pH indicator. The sensors are positioned across the width of the article such that the sensors are in fluid communication with the urine when provided by a wearer of the article. At least one of the sensors is capable of indicating the presence or absence of urine and at least one of the sensors is capable of indicating impending leakage of urine from the article. The presence or absence of urine in the absorbent article and whether or not leakage of urine from the article is impending is determined by observing one or more of the sensors.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figure in which.

Repeat use of reference characters in the present specification and drawings is intended to represent same or analogous features or elements of the disclosure.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to absorbent articles with impending leakage sensors. The absorbent articles described herein provide a simple, user-friendly, cost-effective approach for rapid determination of absorbent capacity so that leakage can be avoided, yet the absorption capacity can be optimally utilized.

Traditionally, wetness sensors that have been positioned in absorbent articles are only able to detect the presence of urine. Such wetness sensors have not been useful in estimating the amount of urine in an article because they are often positioned in the center of the article. For instance, a wetness sensor can be triggered by only a single urination event of a small amount of urine if the urination position is close to the sensor. By contrast, the same sensor may take many urination events with a large amount of urine to be triggered if the urination position is far from the sensor. An objective of the present invention is to provide a means to communicate to a user or caregiver when the absorbent article is close to leakage, but has not yet leaked.

The present inventor has discovered that by utilizing a plurality of wetness sensors along the width of an absorbent article, a determination can be made as to not only the presence or absence of urine, but also as to the remaining absorbent capacity of the article.

For example, in one embodiment of the present disclosure, an absorbent article includes a plurality of sensors integrated therein across the width of the article. The sensors are positioned such that activation of one sensor indicates that the absorbent article has remaining capacity while activation of both sensors indicates that the absorbent article has reached a certain capacity of urine, such as an impending leakage capacity.

In this regard, the exact amount of urine in an absorbent article can be difficult to ascertain. However, it has been determined that generally, as urine fills an absorbent article, the tendency is for the article to fill from the target area towards the distal ends of the article, such as outwards from the central region of the article along the width of the article.

As the amount of urine in the article increases, the intake time can increase while the capacity decreases and, therefore, the propensity to leak can increase. In accordance with the present disclosure, the liquid front position of the urine can be approximately correlated with the amount of urine in the article and a leakage probability can be estimated. Such a estimation can be done with any suitable absorbent article described herein by adding liquid to an article and tracking the liquid front until the maximum absorbent capacity is reached, which will be evident because after the maximum absorbent capacity is reached, leakage will occur. Depending on the leakage probability, impending leakage can be determined. Such a leakage probability can accurately predict whether a leak is imminent based on how far the urine has traveled in the article.

The exact amount of liquid at various locations in an absorbent product is a function of the position of the product during use and wearer to a certain extent. However, in general, as liquid fills the absorbent product, the tendency is for the product to fill from the target area towards the distal ends of the product. It is also known that as the amount of liquid in the product increases, the intake time increases and therefore the propensity to leak increases. The idea then is to correlate the liquid front position with a certain amount of liquid in the product which would translate into a leakage probability. If one were to desire to maintain the leakage probability below 5%, for example, the equivalent product liquid loading level is identified. This is subsequently translated into positions on the product where color change indicators may be positioned. When these are triggered the consumer is alerted to impending leakage. Multiple markings are also possible (1%, 5% etc) to provide the consumer with greater information.

The leakage probability can be predetermined for an absorbent article and sensors can be positioned based on leakage probability. When urine travels a certain distance that has been correlated to a leakage probability, the sensor can detect the urine at that distance and indicate the leakage probability. For instance, in certain embodiments of the present disclosure, one or more sensors are positioned on the basis of leakage probability so that when urine contacts such sensor, a predetermined probability of leakage exists. Multiple sensors can be positioned in multiple locations having different predetermined probabilities of leakage. In certain embodiments, a predetermined probability of leakage can be greater than about 80%, such as about 90%, while in other embodiments, a predetermined probability of leakage is about 95%, while in still other embodiments, a predetermined probability of leakage is about 99%.

As described previously, a plurality of sensors is present in the absorbent articles of the present disclosure in order to detect urine and allow for accurate prediction of the likelihood of leakage. The sensors can be any suitable sensors as would be known in the art and various different types of sensors can be utilized in the same absorbent article if so desired. For example, conventional wetness sensors can be utilized in accordance with the present disclosure. The sensors are positioned across the width of the absorbent article.

As used herein, "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Figure 1:
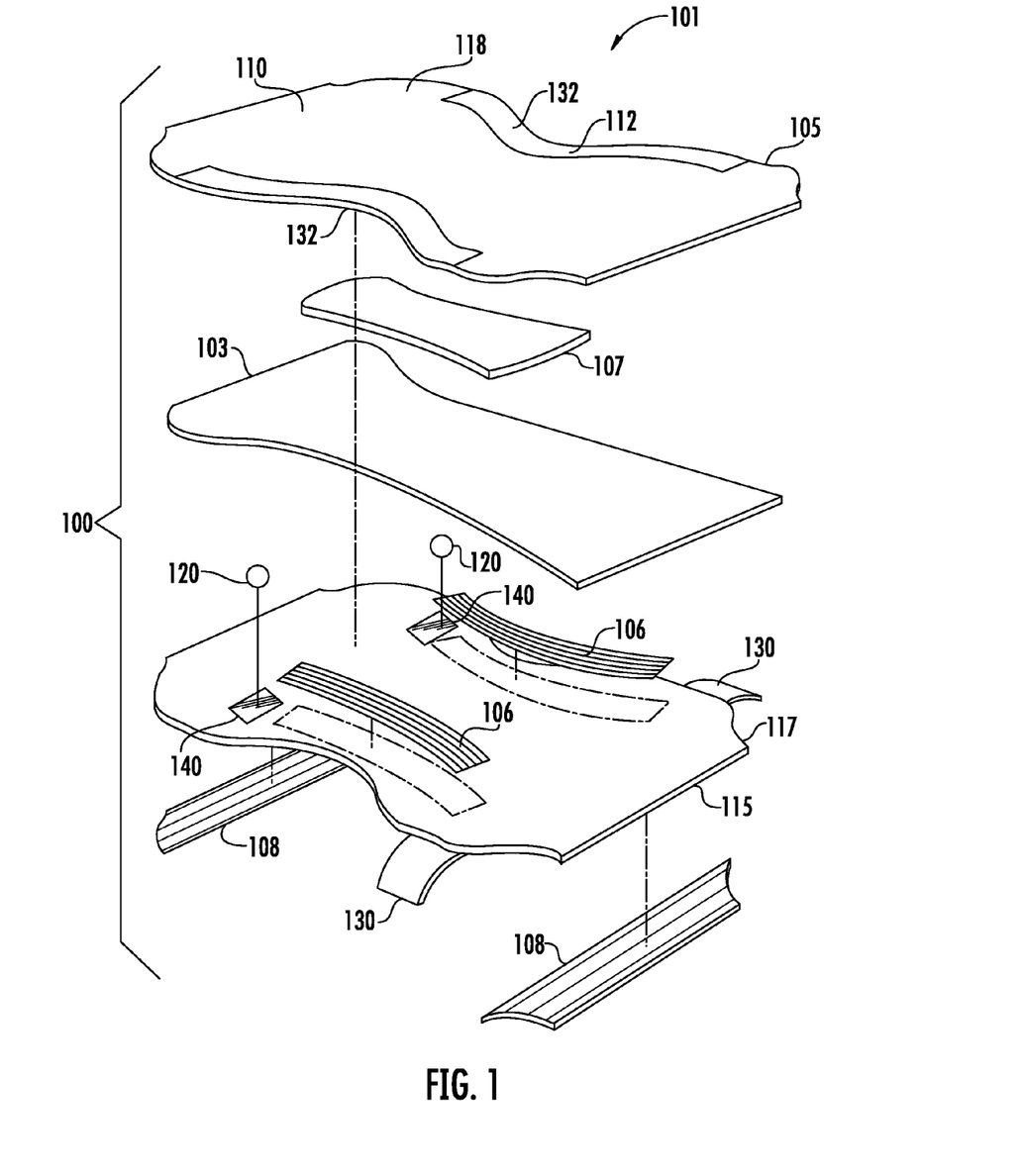
FIG. 1 is a perspective view of one embodiment of an absorbent article of the present disclosure.

Various embodiments of an absorbent article that can be formed according to the present disclosure will now be described in more detail. For purposes of illustration only, an absorbent article is shown in FIG. 1 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present disclosure. Likewise, one or more of the layers referred to in FIG. 2 can also be eliminated in certain exemplary embodiments of the present disclosure.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. No. 5,192,606 to Proxmire, et al.; U.S. Pat. No. 5,702,377 to Collier, IV, et al.; U.S. Pat. No. 5,931,823 to Stokes, et al.; U.S. Pat. No. 6,060,638 to Paul, et al.; and U.S. Pat. No. 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Bishop et al. and U.S. Pat. No. 5,490,846 to Ellis, et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown) that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present disclosure. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 1, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 1, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer.

Figure 2A:
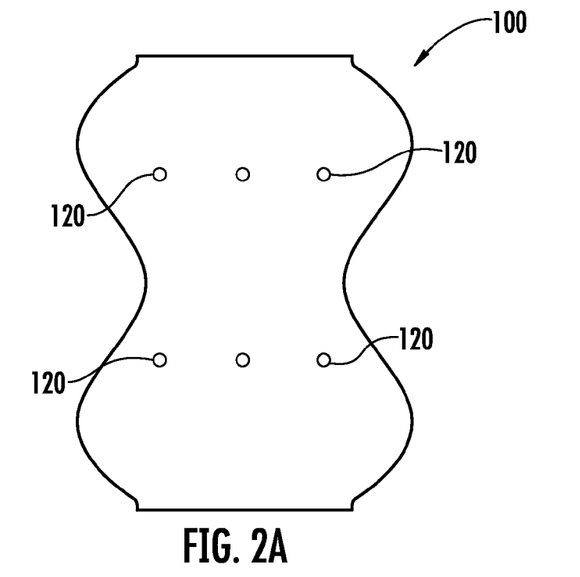
FIGS. 2A-2C are perspective views of certain embodiments of an absorbent article of the present disclosure.
Figure 2B:
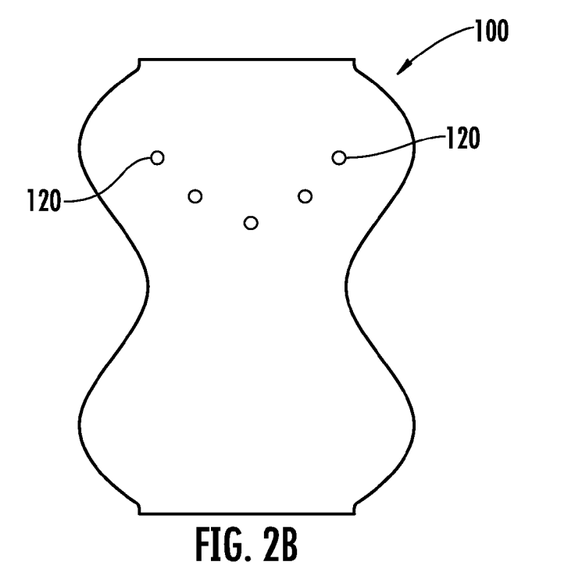
Figure 2C:
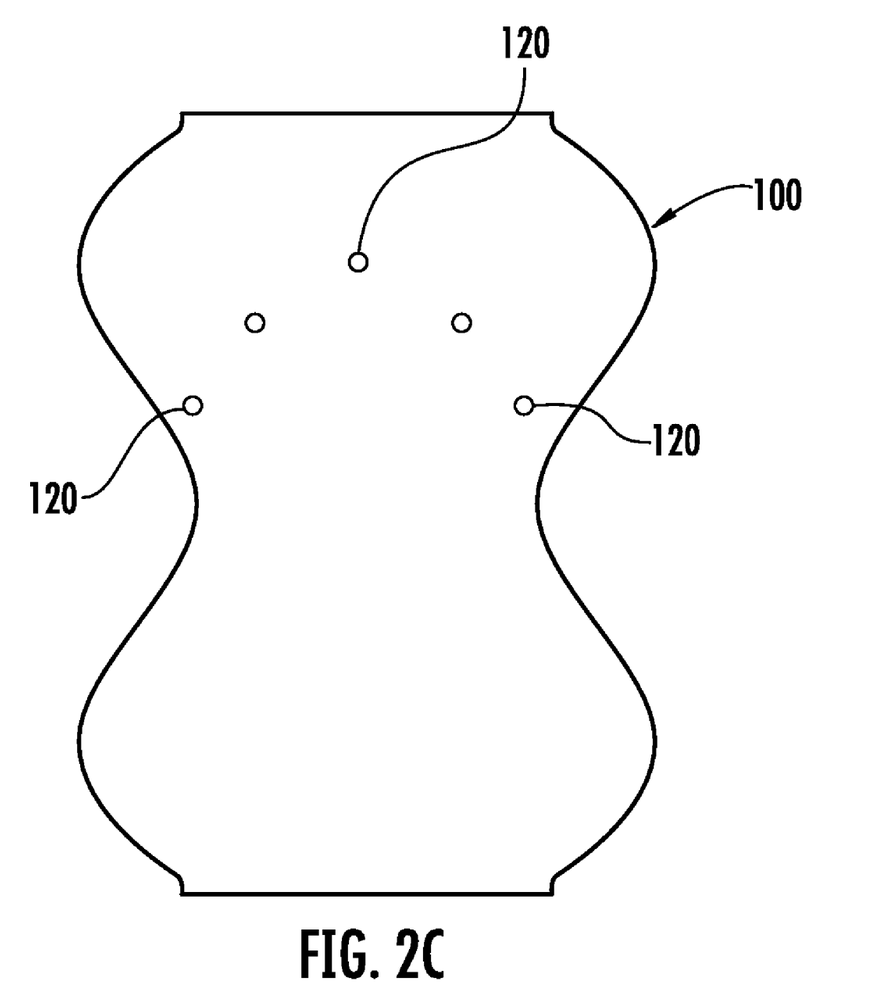

The diaper 101 can also include one or more fasteners 130. For example, two flexible fasteners 130 are illustrated in FIG. 2 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

Generally speaking, the sensors of the present disclosure can be incorporated into the absorbent article in a variety of different orientations and configurations. In this regard, it has been determined that sensors integrated into the absorbent article across the width of the article and positioned such that the sensors are in fluid communication with urine can indicate the presence or absence of urine as well as impending leakage of urine from the article.

Turning back to FIG. 1, one embodiment of the present disclosure is illustrated in which the sensors 120 are generally aligned in a row across the width of the diaper 101. The sensors 120 can be visible to the user or caregiver so that a simple, accurate, and rapid indication of wetness can be provided. The visibility can be accomplished in a variety of ways. For example, in some embodiments, the absorbent article can include a transparent or translucent portion 140 (e.g., window, film, etc.) that allows the sensors to be readily viewed without removal of the absorbent article from the wearer and/or without disassembly of the absorbent article. In other embodiments, the sensors can extend through a hole or aperture in the absorbent article for observation. In still other embodiments, the sensors can simply be positioned on a surface of the absorbent article for observation.

The sensors can be positioned in any suitable arrangement laterally across the width of the article (e.g., the diaper pad). According to certain alternative embodiments, the present inventive concept avoids the center line along the longitudinal axis of the absorbent article. The sensors can form either a straight line, a wave, or a curved line (e.g., parabolic or Ω-like shape in some embodiments) across the front and/or back of the pad. Referring to FIGS. 2A-C, various embodiments of the absorbent article of the present disclosure are illustrated. In an embodiment, the ends of the line of sensors curves toward the leg holes along each longitudinal side, with the center of the curve farther from to the center of the insult area, or in other embodiments the reverse, with the center of the curve closer to the insult area. For instance, in FIG. 2A the sensors 120 are positioned in multiple rows across the width of the article, the rows being substantially parallel to one another. Turning to FIG. 2B, the sensors 120 are positioned so as to form a curved line with the center of the curve closest to the center of the insult area. In FIG. 2C, the sensors 120 are positioned so as to form a curved line with the center of the curve farther from the center of the insult area. In another embodiments, one can have two parallel rows of sensors, each front and back. When the absorbent article diaper is laid out flat, the nearest location of a sensor is at least 50% the distance from the center of the absorbent core area of the article. The distance is greater than or equal to 50% of the total dimension of the absorbent article along its longitudinal axis. Indicator color can change from one to another: either from colored to no color, or from no color to colored. A semi-transparent layer can be present over a background colored design.

It should be understood that any suitable arrangement of the sensors is contemplated by the present disclosure so long as the sensors are arranged along the width of the absorbent article. The sensors can form a straight line, a wave, a curved line such as a parabolic line, or the like. In addition, the sensors can be positioned any suitable distance from one other or from other portions of the absorbent article. For example, in certain embodiments at least one of the plurality of sensors is positioned less than 5 cm from each leg opening of the absorbent article. In still other embodiments, at least one of the plurality of sensors is positioned less than 2 cm from each leg opening of the absorbent article.

As indicated previously, a plurality of sensors can be utilized in accordance with the present disclosure. For example, in certain embodiments, 2 sensors can be utilized. In still other embodiments, 3 sensors can be utilized, while in still other embodiments, greater than 3 sensors can be utilized.

Regardless of the particular manner in which they are integrated, urine can be directly discharged to a portion of the sensors, a liquid permeable cover or other material surrounding the sensors, or can be discharged onto a component of the absorbent article into which the sensors 120 have been integrated.

As discussed above, any suitable sensor can be utilized in connection with the present disclosure. Certain embodiments of sensors that can be formed according to the present disclosure will now be described in more detail.

A sensor in accordance with the present disclosure can include a substrate made from any of a variety of materials through which the urine is capable of passing. For example, the substrate can be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer substrate, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. In one particular embodiment, the substrate is formed from a Biodyne® Plus membrane made by Pall Corporation.

The size and shape of the substrate can generally vary as is readily recognized by those skilled in the art. For instance, the substrate can have a length and width of from about 10 to about 100 millimeters, in some embodiments from about 20 to about 80 millimeters, and in some embodiments, from about 40 to about 60 millimeters. The thickness of the substrate can be less than about 500 micrometers, in some embodiments less than about 250 micrometers, and in some embodiments, less than about 150 micrometers.

To initiate detection of the presence or absence of urine, urine is applied to a portion of the substrate 22. To facilitate detection of urine, a pH indicator can be non-diffusively immobilized on the substrate. The pH indicator can be applied directly to the substrate or first formed into a solution prior to application. Various solvents can be utilized to form the solution, such as, but not limited to, acetonitrile, dimethylsulfoxide (DMSO), ethyl alcohol, dimethylformamide (DMF), and other polar organic solvents. The amount of the pH indicator in the solution can range from about 0.001 to about 100 milligrams per milliliter of solvent, and in some embodiments, from about 0.1 to about 10 milligrams per milliliter of solvent. The pH indicator concentration can be selectively controlled to provide the desired level of detection sensitivity.

In certain embodiments, it is desired that the pH indicator be applied in a manner so that it does not substantially diffuse through the substrate (i.e., non-diffusively immobilized). The pH indicator is configured to have a color transition when exposed to pH levels that are within the range of typical pH for urine (either greater than about 5 or less than about 10). The pH indicator produces an initial color based on a pH outside of the range of typical pH for urine (less than about 5 or greater than about 10). Once the urine sample contacts the pH indicator, the pH changes to induce a color change in the pH indicator signaling that urine has contacted the substrate.

For instance, in certain embodiments, phthalein chromogens constitute one class of suitable pH-sensitive chromogens that can be employed in the present disclosure. Phenol Red (i.e., phenolsulfonephthalein), for example, exhibits a transition from yellow to red over the pH range 6.6 to 8.0. Above a pH of about 8.1, Phenol Red turns a bright pink (fuchsia) color. Derivatives of Phenol Red can also be suitable for use in the present disclosure, such as those substituted with chloro, bromo, methyl, sodium carboxylate, carboxylic acid, hydroxyl and amine functional groups. Exemplary substituted Phenol Red compounds include, for instance, Meta-cresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',3",5',5"-tetrabromophenolsulfonephthalein), Bromochlorophenol Blue (the sodium salt of dibromo-5',5"-dichlorophenolsulfonephthalein), Bromocresol Purple (5',5"-dibromo-ortho-cresolsulfonephthalein), Bromocresol Green (3',3",5',5"-tetrabromo-ortho-cresolsulfonephthalein), and so forth. Still other suitable phthalein chromogens are well known in the art, and can include Bromothymol Blue, Thymol Blue, Bromocresol Purple, thymolphthalein, and phenolphthalein (a common component of universal indicators). For example, Bromothymol Blue exhibits a transition from yellow to blue over a pH range of about 6.0 to 7.6; thymolphthalein exhibits a transition from colorless to blue over a pH range of about 9.4 to 10.6; phenolphthalein exhibits a transition from colorless to pink over a pH range of about 8.2 to 10.0; Thymol Blue exhibits a first transition from red to yellow over a pH range of about 1.2 to 2.8 and a second transition from yellow to blue over a pH range of 8.0 to 9.6; Bromophenol Blue exhibits a transition from yellow to violet over a pH range of about 3.0 to 4.6; Bromocresol Green exhibits a transition from yellow to blue over a pH range of about 3.8 to 5.4; and Bromocresol Purple exhibits a transition from yellow to violet over a pH of about 5.2 to 6.8.

Anthraquinones constitute another suitable class of pH-sensitive chromogens for use in the present disclosure. Anthraquinones have the following general structure:

The numbers 1-8 shown in the general formula represent a location on the fused ring structure at which substitution of a functional group can occur. Some examples of such functional groups that can be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, hydroxy groups, phosphorous groups, etc. Functional groups that result in an ionizing capability are often referred to as "chromophores." Substitution of the ring structure with a chromophore causes a shift in the absorbance wavelength of the compound. Thus, depending on the type of chromophore (e.g., hydroxyl, carboxyl, amino, etc.) and the extent of substitution, a wide variety of quinones can be formed with varying colors and intensities. Other functional groups, such as sulfonic acids, can also be used to render certain types of compounds (e.g., higher molecular weight anthraquinones) water-soluble.

Some suitable anthraquinones that can be used in the present disclosure, as classified by their "CI" number, include Acid Black 48, Acid Blue 25 (D&C Green No. 5), Acid Blue 40, Acid Blue 41, Acid Blue 45, Acid Blue 80, Acid Blue 129, Acid Green 25, Acid Green 27, Acid Green 41, Acid Violet 43, Mordant Red 11 (Alizarin), Mordant Black 13 (Alizarin Blue Black B), Mordant Red 3 (Alizarin Red S), Mordant Violet 5 (Alizarin Violet 3R), Alizarin Complexone, Natural Red 4 (Carminic Acid), Disperse Blue 1, Disperse Blue 3, Disperse Blue 14, Natural Red 16 (Purpurin), Natural Red 8, Reactive Blue 2 (Procion Blue HB), Reactive Blue 19 (Remazol Brilliant Blue R); Alizarin, Alizarin Yellow R, Alizarin Yellow GG, Alizarin S, Nuclear Fast Red, Quinalizarin, Emodin, amino-4-hydroxyanthraquinone, and so forth. For instance, carminic acid exhibits a first transition from orange to red over a pH range of about 3.0 to 5.5 and a second transition from red to purple over a pH range of about 5.5 to 7.0. Alizarin Yellow R, on the other hand, exhibits a transition from yellow to orange-red over a pH range of about 10.1 to 12.0.

Yet another suitable class of pH-sensitive chromogens that can be employed is aromatic azo compounds having the general structure:

wherein, $R_1$ is an aromatic group;

$R_2$ is selected from the group consisting of aliphatic and aromatic groups; and X and Y are independently selected from the group consisting of hydrogen, halides, $-NO_2$, $-NH_2$, aryl groups, alkyl groups, alkoxy groups, sulfonate groups, $-SO_3H$, $-OH$, $-COH$, $-COOH$, halides, etc. Also suitable are azo derivatives, such as azoxy compounds ($X-R_1-N=NO-R_2-Y$) or hydrazo compounds ($X-R_1-NH-NH-R_2-Y$). Particular examples of such azo compounds (or derivatives thereof) include Methyl Violet, Methyl Yellow, Methyl Orange, Methyl Red, and Methyl Green. For instance, Methyl Violet undergoes a transition from yellow to blue-violet at a pH range of about 0 to 1.6, Methyl Yellow undergoes a transition from red to yellow at a pH range of about 2.9 to 4.0, Methyl Orange undergoes a transition from red to yellow at a pH range of about 3.1 to 4.4, and Methyl Red undergoes a transition from red to yellow at a pH range of about 4.2 to 6.3.

Arylmethanes (e.g., diarylmethanes and triarylmethanes) constitute still another class of suitable pH-sensitive chromogens for use in the present disclosure. Triarylmethane leuco bases, for example, have the following general structure:

wherein R, R', and R" are independently selected from substituted and unsubstituted aryl groups, such as phenyl, naphthyl, anthracenyl, etc. The aryl groups can be substituted with functional groups, such as amino, hydroxyl, carbonyl, carboxyl, sulfonic, alkyl, and/or other known functional groups. Examples of such triarylmethane leuco bases include Leucomalachite Green, Pararosaniline Base, Crystal Violet Lactone, Crystal Violet Leuco, Crystal Violet, CI Basic Violet 1, CI Basic Violet 2, CI Basic Blue, CI Victoria Blue, N-benzoyl leuco-methylene, etc. Likewise suitable diarylmethane leuco bases can include 4,4'-bis(dimethylamino)benzhydrol (also known as "Michler's hydrol"), Michler's hydrol leucobenzotriazole, Michler's hydrol leucomorpholine, Michler's hydrol leucobenzenesulfonamide, etc. In one particular embodiment, the chromogen is Leucomalachite Green Carbinol (Solvent Green 1) or an analog thereof, which is normally colorless and has the following structure:

Under acidic conditions, one or more free amino groups of the Leucomalachite Green Carbinol form can be protonated to form Malachite Green (also known as Aniline Green, Basic Green 4, Diamond Green B, or Victoria Green B), which has the following structure:

Malachite Green typically exhibits a transition from yellow to blue-green over a pH range 0.2 to 1.8. Above a pH of about 1.8, malachite green turns a deep green color.

Still other suitable pH-sensitive chromogens that can be employed include Congo Red, Litmus (azolitmin), Methylene Blue, Neutral Red, Acid Fuchsin, Indigo Carmine, Brilliant Green, Picric acid, Metanil Yellow, m-Cresol Purple, Quinaldine Red, Tropaeolin OO, 2,6-dinitrophenol, Phloxine B, 2,4-dinitrophenol, 4-dimethylaminoazobenzene, 2,5-dinitrophenol, 1-Naphthyl Red, Chlorophenol Red, Hematoxylin, 4-nitrophenol, nitrazine yellow, 3-nitrophenol, Alkali Blue, Epsilon Blue, Nile Blue A, universal indicators, and so forth. For instance, Congo Red undergoes a transition from blue to red at a pH range of about 3.0 to 5.2, Litmus undergoes a transition from red to blue at a pH range of about 4.5 to 8.3, and Neutral Red undergoes a transition from red to yellow at a pH range of about 11.4 to 13.0.

However, any suitable pH indicator as would be known in the art is contemplated for use in the present disclosure.

In certain embodiments, the initial color of the immobilized pH indicator can be easily adjusted by immobilizing the indicator along with a pH adjuster, either an acid, a buffer, a base or some combination thereof. The initial color is important to provide a sharp color contrast as large as possible. For instance, when bromothymol blue is used as an indicator, basic condition gives the indicator zone a vivid green color, which is clearly distinguishable from yellow color under slightly acidic condition.

Additionally, other suitable pH adjusters can include mineral acids, sulfonic acids (e.g., 2-[N-morpholino]ethane sulfonic acid ("MES"), carboxylic acids, and polymeric acids. Specific examples of suitable mineral acids are hydrochloric acid, nitric acid, phosphoric acid, and sulfuric acid. Specific examples of suitable carboxylic acids are citric acid, glycolic acid, lactic acid, acetic acid, maleic acid, gallic acid, malic acid, succinic acid, glutaric acid, benzoic acid, malonic acid, salicylic acid, gluconic acid, and mixtures thereof. Specific examples of suitable polymeric acids include straight-chain poly(acrylic) acid and its copolymers (e.g., maleic-acrylic, sulfonic-acrylic, and styrene-acrylic copolymers), crosslinked polyacrylic acids having a molecular weight of less than about 250,000, poly(methacrylic) acid, and naturally occurring polymeric acids such as carageenic acid, carboxymethyl cellulose, and alginic acid. Again, the pH adjuster results in an initial pH outside the range of typical pH for urine (either less than about 5 or greater than about 10) whereby the pH indicator is capable of a color transition when brought into contact with urine.

It is desired that the pH indicator be applied in a manner so that it does not substantially diffuse through the substrate (i.e., non-diffusively immobilized). This enables a user to readily detect the change in color that occurs upon reaction of the pH indicator with the urine and also prevents the pH indicator from leaching out of the substrate. The immobilization can be achieved by many methods such as chemical bonding, physical absorption, or using a carrier such as a polymer or a particle. In one preferred embodiment, a highly charged porous material can effectively immobilize an oppositely charged indicator. In this regard, useful charged porous substrates can include nylon membranes such as Biodyne® Plus from Pall Corporation. Porous non-woven materials such as paper tissues treated with Kymene® have also been found to be suitable charged materials to immobilize negatively charged indicators.

In certain embodiments of the present disclosure, a crosslinked network containing the pH indicator is formed on the substrate of the sensor described herein. Without intending to be limited by theory, it is believed that the crosslinked network can help durably secure the pH indicator, thereby allowing a user to more readily detect a change in its color during use. The crosslinked network can contain "intra-cross links" (i.e., covalent bonds between functional groups of a single molecule) and/or "inter-cross links" (i.e., covalent bonds between different molecules, e.g., between two pH indicator molecules or between a pH indicator molecule and the substrate surface). Crosslinking can be carried out via self crosslinking of the indicator and/or through the inclusion of a separate crosslinking agent. Suitable crosslinking agents, for instance, can include polyglycidyl ethers, such as ethylene glycol diglycidyl ether and polyethylene glycol diglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); aminoxy groups (e.g., dimethylaminoxy and diethylaminoxy); and amide groups (e.g., N-methylacetamide and N-ethylacetamide).

Any of a variety of different crosslinking mechanisms can be employed in the present disclosure, such as thermal initiation (e.g., condensation reactions, addition reactions, etc.), electromagnetic radiation, and so forth. Some suitable examples of electromagnetic radiation that can be used in the present disclosure include, but are not limited to, electron beam radiation, natural and artificial radio isotopes (e.g., α, β, and γ rays), x-rays, neutron beams, positively-charged beams, laser beams, ultraviolet, etc. Electron beam radiation, for instance, involves the production of accelerated electrons by an electron beam device. Electron beam devices are generally well known in the art. For instance, in one embodiment, an electron beam device can be used that is available from Energy Sciences, Inc., of Woburn, Mass. under the name "Microbeam LV." Other examples of suitable electron beam devices are described in U.S. Pat. No. 5,003,178 to Livesay; U.S. Pat. No. 5,962,995 to Avnery; U.S. Pat. No. 6,407,492 to Avnery, et al., which are incorporated herein in their entirety by reference thereto for all purposes. The wavelength λ of the radiation can vary for different types of radiation of the electromagnetic radiation spectrum, such as from about $10^{-14}$ meters to about $10^{-5}$ meters. Electron beam radiation, for instance, has a wavelength λ of from about $10^{-13}$ meters to about $10^{-9}$ meters. Besides selecting the particular wavelength λ of the electromagnetic radiation, other parameters can also be selected to control the degree of crosslinking. For example, the dosage can range from about 0.1 megarads (Mrads) to about 10 Mrads, and in some embodiments, from about 1 Mrads to about 5 Mrads.

The source of electromagnetic radiation can be any radiation source known to those of ordinary skill in the art. For example, an excimer lamp or a mercury lamp with a D-bulb can be used. Other specialty-doped lamps that emit radiation at a fairly narrow emission peak can be used with photoinitiators which have an equivalent absorption maximum. For example, the V-bulb, available from Fusion Systems, is another suitable lamp for use. In addition, specialty lamps having a specific emission band can be manufactured for use with one or more specific photoinitiators.

Initiators can be employed in some embodiments that enhance the functionality of the selected crosslinking technique. Thermal initiators, for instance, can be employed in certain embodiments, such as azo, peroxide, persulfate, and redox initiators. Representative examples of suitable thermal initiators include azo initiators such as 2,2'-azobis(2,4-dimethylvaleronitrile), 2,2'-azobis(isobutyronitrile), 2,2'-azobis-2-methylbutyronitrile, 1,1'-azobis(1-cyclohexanecarbonitrile), 2,2'-azobis(methyl isobutyrate), 2,2'-azobis(2-amidinopropane)dihydrochloride, and 2,2'-azobis(4-methoxy-2,4-dimethylvaleronitrile); peroxide initiators such as benzoyl peroxide, acetyl peroxide, lauroyl peroxide, decanoyl peroxide, dicetyl peroxydicarbonate, di(4-t-butylcyclohexyl)peroxydicarbonate, di(2-ethylhexyl)peroxydicarbonate, t-butylperoxypivalate, t-butylperoxy-2-ethylhexanoate, and dicumyl peroxide; persulfate initiators such as potassium persulfate, sodium persulfate, and ammonium persulfate; redox (oxidation-reduction) initiators such as combinations of the above persulfate initiators with reducing agents such as sodium metabisulfite and sodium bisulfite, systems based on organic peroxides and tertiary amines, and systems based on organic hydroperoxides and transition metals; other initiators such as pinacols; and the like (and mixtures thereof). Azo compounds and peroxides are generally preferred. Photoinitiators can likewise be employed, such as substituted acetophenones, such as benzyl dimethyl ketal and 1-hydroxycyclohexyl phenyl ketone; substituted alpha-ketols, such as 2-methyl-2-hydroxypropiophenone; benzoin ethers, such as benzoin methyl ether and benzoin isopropyl ether; substituted benzoin ethers, such as anisoin methyl ether; aromatic sulfonyl chlorides; photoactive oximes; and so forth (and mixtures thereof). Other suitable photoinitiators can be described in U.S. Pat. No. 6,486,227 to Nohr, et al. and U.S. Pat. No. 6,780,896 to MacDonald, et al., both of which are incorporated herein by reference.

Although not required, additional components can also be employed within the crosslinked network to facilitate the securement of the pH indicator. For example, an anchoring compound can be employed that links the pH indicator to the surface of substrate and further improves the durability of the pH indicator on the sensor. Typically, the anchoring compound is larger in size than the pH indicator, which improves its likelihood of remaining on the surface of the chromatographic medium during use. For example, the anchoring compound can include a macromolecular compound, such as a polymer, oligomer, dendrimer, particle, etc. Polymeric anchoring compounds can be natural, synthetic, or combinations thereof. Examples of natural polymeric anchoring compounds include, for instance, polypeptides, proteins, DNA/RNA and polysaccharides (e.g., glucose-based polymers). Examples of synthetic polymeric anchoring compounds include, for instance, polyacrylic acid and polyvinyl alcohols. One particular example of a polysaccharide anchoring compound is activated dextran. In some embodiments, the anchoring compound can be a particle (sometimes referred to as a "bead" or "microbead"). Naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., can be used. Further, synthetic particles can also be utilized. For example, in one embodiment, latex microparticles are utilized. Although any synthetic particle can be used, the particles are typically formed from polystyrene, butadiene styrenes, styreneacrylic-vinyl terpolymer, polymethylmethacrylate, polyethyl methacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. When utilized, the shape of the particles can generally vary. In one particular embodiment, for instance, the particles are spherical in shape. However, it should be understood that other shapes are also contemplated such as plates, rods, discs, bars, tubes, irregular shapes, etc. In addition, the size of the particles can also vary. For instance, the average size (e.g., diameter) of the particles can range from about 0.1 nanometers to about 1,000 microns, in some embodiments, from about 0.1 nanometers to about 100 microns, and in some embodiments, from about 1 nanometer to about 10 microns.

The manner in which the anchoring compound is used to link the pH indicator and the substrate can vary. In one embodiment, for instance, the anchoring compound is attached to the pH indicator prior to application of both to the substrate. In other embodiments, the anchoring compound can be bonded to the substrate prior to application of the pH indicator. In still other embodiments, the materials can be applied as separate components to the substrate and attachment reactions can take place in situ, optionally at the same time as the crosslinking of the network. For instance, the pH indicator can bind the anchoring compound, the anchoring compound can bind the substrate, and simultaneously, crosslinking reactions can take place between anchoring compounds, between indicators, or between the two. In one such embodiment, the cross-linked network thus formed can be physically held on the substrate without the need for bonding between the substrate and the other components of the system. In particular, the crosslinked network, portions of which can extend within and among the pores of the substrate, can be physically constrained on the substrate, even without specific bonds forming between the substrate and the components of the crosslinked network.

In the case of bonds being formed between the sensor components, attachment of the anchoring compound to a substrate as well as attachment of the anchoring compound to the pH indicator can be accomplished using carboxylic, amino, aldehyde, bromoacetyl, iodoacetyl, thiol, epoxy or other reactive functional groups, as well as residual free radicals and radical cations, through which a binding reaction can be accomplished and according to any suitable methods, e.g., thermal processes, photo-initiated processes, catalyzed reactions, and the like. For example, a substrate can be amine-functionalized through contact with an amine-containing compound, such as 3-aminopropyltriethoxy silane, to increase the amine functionality of the surface and bind the anchoring compound to the surface via, e.g., aldehyde functionality of the anchoring compound. A surface functional group can also be incorporated on a particle-type anchoring compound as a reactive functionality, for instance when the surface of the particle contains a relatively high surface concentration of polar groups. In certain cases, the particle can be capable of direct bonding to substrate and/or a pH indicator without the need for further modification.

It should be understood that, besides covalent bonding, other attachment techniques, such as charge-charge interactions, can also be utilized for attaching the anchoring compound to the chromatographic medium and/or for attaching the pH indicator to the anchoring compound. For instance, a charged anchoring compound, such as a positively charged polyelectrolyte anchoring compound, can be immobilized on a negatively charged substrate, such as negatively charged porous nitrocellulose membrane, through charge-charge interactions between the two. Similarly, a negatively charged indicator, such as a diazonium ion, can be immobilized on a positively charged anchoring compound.

The sensors of the present disclosure can include indicia to indicate to a user the presence or absence of urine or the impending leakage of urine from the article. For example, the indicia can include numerical values or graphics that illustrate impending leakage. In certain embodiments, the indicia can include a numerical value for the predetermined probability of leakage, discussed previously. In such embodiments, the indicia can indicate a percentage probability of leakage.

In certain embodiments, sensors made in accordance with the present disclosure are able to maintain signal strength for at least about 10 minutes, more particularly at least about 30 minutes, more particularly at least about 1 hour. Additionally, such sensors can be subjected to multiple urine insults and still produce accurate test results.

One particular embodiment of a method for detecting the presence or absence of urine as well as impending leakage of urine in an absorbent article will now be described in more detail. Initially, urine is contacted with an absorbent article as described herein having a plurality of sensors being integrated into the article across the width of the article. The sensors are positioned such that they are in fluid communication with the urine when provided by a wearer of the article. At least one of the sensors is capable of indicating the presence or absence of urine and at least one of the sensors is capable of indicating impending leakage of urine from the article. The presence or absence of urine in the absorbent article as well as whether or not leakage of urine is impending can be determined by observing one or more of the sensors.

In summary, the present disclosure provides a relatively simple and cost-efficient absorbent article for accurately detecting the presence or absence of urine as well as impending leakage or urine from an absorbent article. The invention involves an absorbent article having a porous inner lining, an absorbent core, an impervious outer cover layer, and a plurality of wetness sensors. The absorbent article has a major and minor dimension, and the sensors are arrayed in a pattern across the minor dimension or width, in a non-longitudinal orientation, of a region proximal to each end of said absorbent article in a manner that each of the sensors activates when a volume of liquid interacts with the sensor, and signals to a user that the absorbent article is approaching its full liquid capacity before leaking. Each of said sensors is in fluid communication with the absorbent core. In certain variations, the sensors are arrayed in at least one row, forming an arc across the minor dimension at each end of the absorbent article. In other variations, the sensors are arrayed in two rows substantially parallel to each other. The sensors are visually observable through the outer cover layer. The sensors can be arrayed in groups of single or plural sensors situated at each corner of the absorbent article. The sensors transition from being a) colored to colorless, b) colorless to colored, c) or from one hue or color to another or color. In other embodiments, the absorbent article has a front panel and a back panel, and the sensors are situated at a location on both front and back panels that is at least a quarter to a third of the cross-sectional dimension of a target absorbent area adapted to receive directly a liquid insult. The absorbent article can be a diaper, training pants, absorbent undergarment, adult incontinence product, or feminine hygiene product.

The invention also encompasses a method of using an indicator to communicate that a personal care absorbent article is near its capacity for containing a given volume of liquid. The method includes: providing an absorbent personal care article having a front panel and a back panel, a plurality of sensors arrayed in a region on said front and back panels that are near distal ends of the article and absent from a central region of the absorbent article; insulting an absorbent region of the article one or more times with a liquid until a portion of the volume of liquid or wetness physically reaches a sensor and interacts with the sensors on both front and back panels to trigger a visually observable signal. The sensors are in fluid communication with an absorbent core. The results can be visible so that they are readily observed by the person with interest in a prompt manner and under test conditions conducive to highly reliable and consistent results.

The present disclosure can be better understood with reference to the following examples.

EXAMPLES

Example 1

1. Wetness sensor I: A piece of Biodyne plus Nylon membrane from Pall Co. was soaked in 0.2 mg/ml of bromocresol green, 2 mg/ml of citric acid, and water for ten minutes and air dried to make wetness sensor I. The sensor strip is yellow and becomes green/blue upon wetting with synthetic urine or urine.

2. Wetness sensor II: Biodyne plus Nylon membrane was soaked in 0.2 mg/ml phloxine B and 0.02 N HCl for ten minutes and air dried to make wetness sensor II. The sensor strip is white and becomes pink upon wetting with synthetic urine or urine.

3. Three holes were made in three Huggies newborn diapers by removing a piece of the outer cover, and locating one hole in each of the centers of the diapers and locating two additional holes 7 cm away from each of the centers. A piece of wetness sensor I was inserted in each of the central holes and taped against the fluff using a piece of tape. A piece of wetness sensor II was inserted in each of the other two holes and taped against the fluff. The wetness sensor I in each diaper acts as a wetness event sensor and each of the two wetness sensors II in each diaper act as sensors for diaper fullness, indicating that the diaper has reached its capacity when both sensors indicate pink color.

4. Three diapers above were laid on a bench and 50 ml synthetic urine was applied to each diaper in a different position, one to the center of the diaper, one 2.5 cm left away from the diaper center and another 2.5 cm right away from the center. The wetness sensor I of all three diapers changed from yellow to green and remained green thirty minutes later. The wetness sensor II remained white for all the three diapers.

Thirty minutes later, each diaper was insulted again with 40 ml more synthetic urine in the same location and no further change was observed except that wetness sensor I became blue. Another thirty minutes later, each diaper was insulted again with 40 ml synthetic urine. Thirty minutes after insult, nothing changed for the diaper insulted in the center, while one of the two wetness sensor II changed to pink in each of the other two diapers. Further addition of 30 ml synthetic urine to each diaper caused all the three wetness sensors in all three diapers to be activated, indicating full capacity was reached.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so further described in such appended claims.

What is claimed is:

1. An absorbent article capable of indicating the presence or absence of urine as well as impending leakage of urine comprising:
    a substantially liquid impermeable layer;
    a liquid permeable layer;
    an absorbent core positioned between the substantially liquid impermeable layer and the liquid permeable layer; and
    a plurality of sensors integrated into the article across the width of the article and positioned such that the sensors are in fluid communication with urine when provided by a wearer of the article, at least one of the sensors comprising a pH indicator, at least one of the sensors being capable of indicating the presence or absence of urine, at least one of the sensors being capable of indicating impending leakage of urine from the article and being positioned on the basis of leakage probability so that when urine contacts such sensor, a predetermined probability of leakage exists.

2. The absorbent article of claim 1, wherein the sensors are generally aligned in a row across the width of the article.

3. The absorbent article of claim 1, wherein the sensors are generally aligned in greater than one row across the width of the article.

4. The absorbent article of claim 3, wherein at least two rows are substantially parallel to one another.

5. The absorbent article of claim 1, wherein the article further comprises two leg openings along a portion of the edges of the article when worn about a wearer, the sensors positioned across the width of the article such that at least one sensor is positioned less than 5 cm from each leg opening.

6. The absorbent article of claim 1, wherein the article further comprises two leg openings along a portion of the edges of the article when worn about a wearer, the sensors positioned across the width of the article such that at least one sensor is positioned less than 2 cm from each leg opening.

7. The absorbent article of claim 1, wherein the predetermined probability of leakage is at least about 99%.

8. The absorbent article of claim 7, wherein the predetermined probability of leakage is at least about 90%.

9. The absorbent article of claim 7, wherein the predetermined probability of leakage is at least about 95%.

10. The absorbent article of claim 7, wherein greater than one sensor is capable of indicating impending leakage of urine from the article, each such sensor being positioned on the basis of leakage probability so that when urine contacts such sensor, a predetermined probability of leakage exists, the predetermined probability of leakage being different for each such sensor.

11. The absorbent article of claim 7, wherein the sensors comprise indicia indicating the predetermined probability of leakage.

12. The absorbent article of claim 1, wherein the pH indicator is capable of a color transition when in contact with urine.

13. The absorbent article of claim 1, wherein the pH indicator comprises bromothymol blue, thymol blue, phenol red, neutral red, bromophenol blue, methyl orange, alizarine yellow R, or combinations thereof.

14. The absorbent article of claim 1, wherein the absorbent article defines one or more windows through which the sensors are observable.

15. The absorbent article of claim 1, wherein the absorbent article comprises a diaper, training pant, absorbent undergarment, adult incontinence article, or feminine hygiene product.

16. The absorbent article of claim 1, wherein the pH indicator is capable of a color transition when in contact with urine.

17. The absorbent article of claim 1, wherein the absorbent article defines one or more windows through which the sensors are observable.

18. A method for detecting the presence or absence of urine as well as impending leakage of urine in an absorbent article comprising:
    contacting urine with an absorbent article, the absorbent article comprising a substantially liquid impermeable layer, a liquid permeable layer, and an absorbent core positioned between the substantially liquid impermeable layer and the liquid permeable layer, a plurality of sensors being integrated into the article across the width of the article and positioned such that the sensors are in fluid communication with the urine when provided by a wearer of the article, at least one of the sensors comprising a pH indicator, at least one of the sensors being capable of indicating the presence or absence of urine, at least one of the sensors being capable of indicating impending leakage of urine from the article and being positioned on the basis of leakage probability so that when urine contacts such sensor, a predetermined probability of leakage exists; and
    determining the presence or absence of urine in the absorbent article and whether or not leakage of urine from the article is impending by observing one or more of the sensors.

19. The absorbent article of claim 18, wherein the predetermined probability of leakage is at least about 99%.

20. The absorbent article of claim 18, wherein the predetermined probability of leakage is at least about 90%.

* * * * *